(12) United States Patent
Novarino et al.

(10) Patent No.: US 10,633,773 B2
(45) Date of Patent: Apr. 28, 2020

(54) NONWOVEN FABRIC AND PROCESS FOR FORMING THE SAME

(71) Applicants: Fitesa Germany GmbH, Peine (DE); Fitesa Sweden AB, Norrköping (SE)

(72) Inventors: Elena Novarino, Hannover (DE); Dag Fohlin, Norrköping (SE)

(73) Assignees: FITESA SWEDEN AB, Norrkoping (SE); FITESA GERMANY GMBH, Peine (DE)

( * ) Notice: Subject to any disclaimer, the term of this patent is extended or adjusted under 35 U.S.C. 154(b) by 0 days.

(21) Appl. No.: 15/540,398

(22) PCT Filed: Nov. 24, 2015

(86) PCT No.: PCT/EP2015/077422
§ 371 (c)(1),
(2) Date: Jun. 28, 2017

(87) PCT Pub. No.: WO2016/107698
PCT Pub. Date: Jul. 7, 2016

(65) Prior Publication Data
US 2018/0002846 A1    Jan. 4, 2018

(30) Foreign Application Priority Data
Jan. 2, 2015  (EP) .................................. 15150009

(51) Int. Cl.
*D04H 1/4291*    (2012.01)
*B32B 7/05*    (2019.01)
(Continued)

(52) U.S. Cl.
CPC ..... *D04H 1/4291* (2013.01); *A61F 13/15707* (2013.01); *A61F 13/513* (2013.01);
(Continued)

(58) Field of Classification Search
CPC .......... A61F 13/15707; A61F 13/51113; A61F 13/5116; A61F 13/513; A61F 2013/51178;
(Continued)

(56) References Cited

U.S. PATENT DOCUMENTS

2004/0005457 A1    1/2004  DeLucia et al.
2012/0251771 A1    10/2012 Wilson et al.

FOREIGN PATENT DOCUMENTS

WO    WO 2006/048173    5/2006
WO    WO 2012/024576    2/2012
(Continued)

OTHER PUBLICATIONS

Extended European Search Report for corresponding European Application No. 15150009.7 dated Jul. 17, 2015, 6 pages.
(Continued)

*Primary Examiner* — Arti Singh-Pandey
(74) *Attorney, Agent, or Firm* — Rimon, P.C.

(57) ABSTRACT

The present invention relates to a nonwoven fabric comprising a plurality of polypropylene-containing fibers that form a nonwoven web, which fibers in addition contain a slip agent, the web has a side which is provided with an alternating pattern which consists of individualized bonded areas which bonded areas are in the form of rods which are arranged in the cross direction of the web, the alternating pattern of individualized bonded areas defines a non-bonded area, the web has a basis weight on the range of from 5-25 g/m², the surface of the bonded areas is in the range of 5-20% of the total surface of the side, and the surface of the non-bonded area is in the range of 80-95% of the total surface of the side. The present invention further relates to a process for forming the nonwoven fabric.

12 Claims, 1 Drawing Sheet calender bonding
rods in CD-direction

(51) Int. Cl.

| | |
|---|---|
| *A61F 13/511* | (2006.01) |
| *A61F 13/15* | (2006.01) |
| *B32B 5/02* | (2006.01) |
| *D04H 1/544* | (2012.01) |
| *B32B 5/08* | (2006.01) |
| *B32B 5/26* | (2006.01) |
| *B32B 5/06* | (2006.01) |
| *A61F 13/513* | (2006.01) |
| *A61L 15/24* | (2006.01) |
| *D04H 1/56* | (2006.01) |
| *D04H 3/007* | (2012.01) |
| *D04H 3/14* | (2012.01) |

(52) U.S. Cl.
CPC ..... *A61F 13/5116* (2013.01); *A61F 13/51113* (2013.01); *A61L 15/24* (2013.01); *B32B 5/022* (2013.01); *B32B 5/06* (2013.01); *B32B 5/08* (2013.01); *B32B 5/26* (2013.01); *B32B 7/05* (2019.01); *D04H 1/544* (2013.01); *D04H 1/56* (2013.01); *D04H 3/007* (2013.01); *D04H 3/14* (2013.01); *A61F 2013/51178* (2013.01); *A61F 2013/51182* (2013.01); *A61F 2013/51316* (2013.01); *A61F 2013/51338* (2013.01); *B32B 2262/0253* (2013.01); *B32B 2262/0276* (2013.01); *B32B 2262/04* (2013.01); *B32B 2262/06* (2013.01); *B32B 2262/12* (2013.01); *B32B 2307/54* (2013.01); *B32B 2307/718* (2013.01); *B32B 2307/726* (2013.01); *B32B 2307/746* (2013.01); *B32B 2555/02* (2013.01)

(58) Field of Classification Search
CPC .. A61F 2013/51182; A61F 2013/51316; A61F 2013/51338; A61L 15/24; B32B 2262/0253; B32B 2262/0276; B32B 2262/04; B32B 2262/06; B32B 2262/12; B32B 2307/54; B32B 2307/718; B32B 2307/726; B32B 2307/746; B32B 2555/02; B32B 5/022; B32B 5/06; B32B 5/08; B32B 5/26; B32B 7/045; D04H 1/4291; D04H 1/544; D04H 1/56; D04H 3/007; D04H 3/14
See application file for complete search history.

(56) References Cited

FOREIGN PATENT DOCUMENTS

| WO | WO 2012/134988 | 10/2012 |
|---|---|---|
| WO | WO 2014/044235 | 3/2014 |

OTHER PUBLICATIONS

International Preliminary Report on Patentability (Chapter II) from International Application No. PCT/EP2015/077422, dated May 10, 2017, 11 pages.
International Search Report and Written Opinion for corresponding International Application No. PCT/EP2015/077422, dated Feb. 9, 2016, 12 pages.

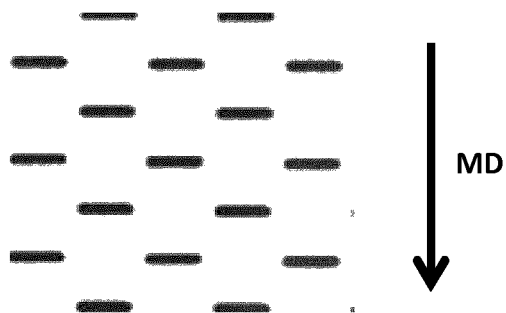
calender bonding rods in CD-direction
MD

NONWOVEN FABRIC AND PROCESS FOR FORMING THE SAME

FIELD OF THE INVENTION

The present invention relates to a nonwoven fabric and a process for forming the nonwoven fabric.

BACKGROUND OF THE INVENTION

Nonwoven fabrics are widely applied in disposable absorbent articles for personal care or hygiene. In such articles the appearance of softness is of great importance since it reassures the wearer or caregiver that the article will be experienced as comfortable.

In WO 2012/024576 A1, an absorbent article adapted to be worn about a wearer's lower torso is described which aims to enhance the perceived softness of the absorbent article. The absorbent article described in said document comprises a liquid permeable top sheet, a liquid impermeable back sheet and an absorbent core disposed between the top sheet and the back sheet. The liquid impermeable back sheet comprises a laminate of a wearer-facing layer of liquid impermeable, vapour permeable polymeric film and a garment-facing layer of a nonwoven web. The nonwoven web is being impressed with a first pattern of bond impressions in the shape of diamonds, which first pattern defines a second pattern of unbounded raised regions which also have the shape of diamonds. In this respect reference is made to FIGS. 3A-4B. In the process for manufacturing the nonwoven web a hydroentangling or hydroengorgement process is required to increase loft and/or calliper, enhancing visual and tactile softness signals. A drawback of such hydroentangling or hydroengorgement process is, however, that it adds considerably to the manufacturing costs of the absorbent articles. Moreover, the softness of said absorbent articles leaves room for improvement.

WO 2006/048173 describes a loop-forming nonwoven material for a mechanical closure system. The fabrics are thermally bonded with a first pattern of bond impressions that create a second pattern of larger unbonded raised regions and a third pattern of smaller unbonded areas. The impressions are a combination of trilobally and linearly shaped geometry. This provides a positive impact on the mechanical stability of the fabric but has the disadvantage that it limits the drapability, an important feature for softness perceiveness.

Object of the present invention is to provide a nonwoven fabric suitable for use in an absorbent article having a simplified pattern of bonded and non-bonded areas which can more easily be manufactured, and which at the same time shows an improved softness.

It is a further object of the present invention to provide a dimensionally stable nonwoven fabric with improved softness, sufficient shear strength, and a high tensile strength.

It is yet another object of the present invention to nonwoven fabrics that can be used as wet and dry wipes.

SUMMARY OF THE INVENTION

It has now been found that this can be established when use is made of a combination of a particular pattern of bonded and non-bonded areas and polypropylene-containing fibers that in addition contain a slip agent.

Accordingly, the present invention relates to a nonwoven fabric comprising a plurality of polypropylene-containing fibers that form a nonwoven web, which fibers in addition contain a slip agent, the web has a side which is provided with an alternating pattern which consists of individualized bonded areas which are in the form of rods which are arranged in the cross direction of the web, the alternating pattern of individualized bonded areas defines a non-bonded area, the web has a basis weight in the range of from 5-25 g/m$^2$, the surface of the bonded areas is in the range of 5-20% of the total surface of the side, and the surface of the non-bonded area is in the range of 80-95% of the total surface of the side.

A major advantage of the present invention resides in the fact that nonwoven fabric is relatively simple to make and that is displays a surprisingly high perceived softness. An additional major advantage is the fact that the present nonwoven fabrics display a surprisingly high perceived softness and at the same time a high tensile strength. This is surprising since it is generally acknowledged that softness and dimensional stability (i.e. high tensile strength) of a thermobonded nonwoven fabric are features that mutually exclude each other.

DETAILED DESCRIPTION OF THE INVENTION

In accordance with the present invention the nonwoven fabric comprises a plurality of polypropylene-containing fibers that form a nonwoven web which comprises a side which is provided with an alternating pattern which consists of individualized bonded areas which are in the form of rods which are arranged in the cross direction of the web. The alternating pattern which consists of individualized bonded areas defines a second pattern of non-bonded areas, and the web has a basis weight in the range of from 5-25 g/cm$^2$, the surface of the bonded areas is in the range of 5-20% of the total surface of the side, and surface of the non-bonded area is in the range of from 80-95% of the total surface of the side. The combination of the particular alternating pattern which consists of individualized bonded areas, polypropylene-containing fibers that in addition contain a slip agent and the high surface of the non-bonded area to be used according to the present invention provides the surprisingly high softness. Moreover, the large non-bonded areas allow for the fiber to bulk up and increase the bulkiness of the fabric. This is perceived as an even higher softness from both visual and the tactile perspective. Preferably, the surface of the non-bonded area is in the range of from 85-92% of the total surface area of the side. More preferably, the surface of the non-bonded area is in the range of from 88-91% of the total surface area of the side. The alternating pattern consists of the individualized bonded areas which are in the form of rods. Hence, the alternating pattern does not contain additional bonded areas in addition to the rods which are arranged in the cross direction of the web.

The surface of the bonded areas is preferably in the range of from 8-15% of the total surface area of the side, more preferably in the range of from 9-12% of the total surface area of the side.

The individualized bonded areas are in the form of rods which are arranged in the cross direction of the web. The cross direction is the direction along the web material substantially perpendicular to the direction of forward travel of the web material through the manufacturing line in which the web material is manufactured.

Preferably, the individualized bonded areas in the form of rods each in their length direction form an angle of 90° with the machine direction of the web.

The rods are preferably arranged in such a way that in the machine direction no uninterrupted regions exist along the web, while in the cross direction the arrangement of the rods define a plurality of uninterrupted regions that extend continuously along the web. Such a preferred arrangement of the rods results in a number of improved fabric properties.

The tensile strength into the cross direction is significantly improved, as the filaments are boldly bound perpendicular to their preferred lay-down direction. It is thereby of importance that no uninterrupted regions in the preferred lay-down direction (i.e. the machine direction) exist, as this would create weak areas of unbonded filaments, resulting in a reduced tensile strength. Moreover, since there are no uninterrupted regions in the machine direction along the web, the free fiber length (i.e. average length of a single fiber between its first and second bond) is comparatively short, resulting in an improved abrasion resistance. Further, this particular arrangement of rods provides uninterrupted unbonded areas in the cross direction, significantly reducing the bending forces of the fabric and translating into an excellent drapability without sacrificing mechanical strength. This finding is surprising because these two properties usually exclude each other.

The width of these uninterrupted regions in the cross direction in this preferred arrangement of rods is suitably larger than 750 µm, and preferably the width is in the range of from 1000-2000 µm.

The rods may have flat ends and/or bended ends. Preferably, the bended ends have a circular shape. Preferably, the rods have a linear shape.

Suitably, the individualized bonded areas in the form of rods have a surface in the range of from 0.7-1.5 mm$^2$, preferably in the range of from 0.9-1.3 mm$^2$, and more preferably in the range of from 1.1-1.2 mm$^2$.

The nonwoven web has a basis weight in the range of from 5-25 g/m$^2$, preferably in the range of from 8-22 g/m$^2$, and more preferably in the range of from 10-20 g/m$^2$.

The rods suitably have a maximum width in the range of from 0.1-1.2 mm, preferably in the range of from 0.3-0.8 mm, and more preferably in the range of from 0.4-0.6 mm.

The rods suitably have a maximum length in the range of from 1.2-3.5 mm, preferably in the range of from 1.8-3.0 mm, and more preferably in the range of from 2.2-2.6 mm.

Suitably, the individualized bonded areas in the form of rods have a length which is 2-10 times, preferably 2-8 times their width.

The discrete non-bonded area suitably has a depth in the range of from 0.1-0.8 mm, preferably in the range of from 0.1-0.6 mm, more preferably in the range of from 0.15-0.5 mm, and most preferably in the range of from 0.15-0.4 mm.

Suitably, the distance between each pair of adjacent rods is in the range of from 1.8-3.0 mm, preferably 2.2-2.6 mm in the cross direction Suitably, distance between each pair of adjacent rods is in the range of from 2.5-5.0 mm, preferably 3.3-4.2 mm in the machine direction In this respect it is observed that the machine direction is the direction along the web material substantially parallel to the direction of forward travel of the web material through the manufacturing line in which the web material is manufactured.

In accordance with the present invention use is made of polypropylene-containing fibers. The nonwoven fabric may also contain fibers made from other thermoplastic polymers such as polyethylene and its copolymers, aliphatic and aromatic polyesters, and combinations thereof. Further, the nonwoven fabrics may also comprise natural fibers such as wood, cotton, or rayon in combination with thermoplastic fibers. The nonwoven web may also be a composite made up of a mixture of two or more different fibers or a mixture of fibers and particles. Suitably, the polypropylene-containing fibers are present in an amount of at least 25 wt %, based on the total amount of fibers in the nonwoven fabric. Preferably, the polypropylene-containing fibers are present in an amount of at least 50 wt %, more preferably at least 75 wt %, based on the total amount of fibers in the nonwoven fabric. Most preferably, the nonwoven fabric only contains polypropylene-containing fibers.

The polypropylene-containing fibers may comprise a polypropylene homopolymer or a polypropylene copolymer. In particularly, the polypropylene copolymers can attractively be used in the present invention. Preferred are polypropylene materials that comprise a propylene-α-olefin copolymer and a propylene homopolymer.

The melt flow rate (MFR) of the polypropylene material to be used in the present invention is suitably less than 90 dg/min. The MFR is determined using ASTM test method D1238, 2.16 kg. Preferably, the MFR of the polyolefin material is in the range of from 15-50 dg/min, more preferably in the range of from 15-35 dg/min.

The polypropylene-containing fibers to be used in accordance with the present invention suitably have a tex of less than 2.5 dtex, preferably less than 2.2 dtex. A tex is metric measure of the weight per unit of a fiber. It is numerically equal to the weight in grams of ten kilometer (10000 meters) of the fiber.

Preferably, the fibers are formed from polyethylene, polypropylene, copolymers of polyethylene and polypropylene, or blends of polyethylene and polypropylene or blends of polypropylene and polyethylene with their copolymers. However, such a mixture contains at least 25 wt %, preferably at least 50 wt % polypropylene, based on the total weight of the mixture. More preferably, the polypropylene-containing fibers only contain a polypropylene material as the thermoplastic component. Suitable examples of polyolefin materials include propylene homopolymers.

In the case of propylene-based polymers, the polymers may comprise comonomer-derived units selected from ethylene and C4-C10 α-olefins.

The polypropylene-containing fibers to be used in accordance with the present invention in addition contain a slip agent. It is the use of a slip agent in combination with the particular pattern of rod and a polypropylene material which brings about the surprisingly high perceived softness.

The slip agent is suitably added to the polypropylene material during the manufacturing process of the fabric, e.g. in form of a masterbatch during the spinning process.

The slip agent to be used in accordance with the present invention can be any slip agent which can suitably be used in the manufacturing of nonwoven fabrics. Suitably, the slip agent is a hydrocarbon compound that preferably contains heteroatoms which create one or more functional groups, for example, oxygen-containing groups such as hydroxy, alkoxys, carboxy, esters, nitrogen-containing groups such as amines, amides, phosphor-containing functional groups, or silicone-containing functional groups. Moreover, also aryl- and functional aryl groups as well as one or more unsaturated C—C-bonds can suitably be present.

Typical examples of specifically attractive slip agents are for example, polyethylene and polypropylene waxes, primary and secondary amides such as for instance erucamide and oleamide, and stearyl derivatives.

The slip agent is suitably present in an amount in the range of from 0.1-5 wt %, preferably in an amount of 0.5-3 wt %, based on the total weight of the polypropylene-containing fibers.

Besides additives already contained in the employed polymers, addition of further additives is possible to provide additional properties to the fibers. Suitable further additives include thermal stabilizers, light stabilizers, waxes, and additives to make the fabrics either hydrophilic or hydrophobic. The addition of filler materials can sometimes also be of advantage. Suitable filler materials include organic and inorganic filler materials. Suitable examples of inorganic filler materials include minerals such as calcium carbonate, metals such as aluminium and stainless steel. Suitable examples of organic filler materials include sugar-based polymers.

In a particularly attractive embodiment of the present invention, the polypropylene-containing fibers contain 98 wt % of a Ziegler-Natta polypropylene, e.g. LyondellBasell's Moplen HP561R, as the polypropylene material and 2 wt % of an erucamide-containing slip additive, e.g. Crodamide ER from Croda Polymer Additives.

Various fiber cross-sections are possible. A round fiber cross-section is preferred, but also tri- and multilobal shaped fibers can also advantageously be used. Other suitable fiber cross-sections include triangular, bone-shaped, moon-shaped, hollow-fibers, and ribbon-shaped cross-sections.

The fibers from which the nonwoven webs are made can suitable be single component or multicomponent fibers such as bicomponent fibers. Suitable examples of multicomponent fibers include symmetric and eccentric core/sheath fibers, side-by-side fibers of NB or A/B/A-structure, segmented pie fibers, island-in-a-sea fibers, and striped fibers. Preferred are bicomponent fibers where the two components are arranged in a symmetric core-sheath way or in a side-by-side way. Most preferred are core-sheath bicomponent fibers comprising a higher melting compound and a lower melting compound, for example polyethylene and polypropylene. In general, for core-sheath fibers, the core comprises the component with the higher melting point and the sheath comprises the component with the lower melting point, but it can be advantageous to have it in the reversed way. In a preferred embodiment, the bicomponent fiber has a core of polypropylene and a sheath of polyethylene. In preferred embodiments, the bicomponent fiber comprises from 10% to 90% by weight of the higher melting component in the core and from 90% to 10% by weight of the lower melting component in the sheath. Most preferably, the bicomponent fiber has from 30% to 70% by weight of the higher melting component in the core. The bicomponent fibers may contain different types of polypropylene. More preferably, the bicomponent fiber has a core of a polypropylene which has a higher melting point and a sheath of a polypropylene which has a lower melting point. In another preferred embodiment, a side-by-side-bicomponent fiber comprises two polypropylenes that differ in melt temperature or melt flow.

The fibers are suitably joined by bonding to form a coherent web structure. Suitable bonding techniques include, but are not limited to, chemical bonding and thermal bonding, for example thermal calendering or bonding by a hot gas stream. Also ultrasonic welding is possible.

The nonwoven fabrics in accordance with the present invention may be produced by any of the known process for making a nonwoven fabric.

The nonwoven fabric may be a single layer or multi-layer nonwoven fabric having, for example, at least one layer of a spunbonded web joined to at least one layer of a meltblown web, a carded web, or other suitable material. Suitably, the nonwoven fabric according to the present invention comprises in addition a second nonwoven web.

The nonwoven webs may be extensible, elastic, or non-elastic. The nonwoven webs may be spunbonded webs, meltblown webs, air-laid webs, or carded webs. If the nonwoven web is a web of meltblown fibers, it may include meltblown microfibers.

The fibers can be made according to spinning technologies known in the art. Most conveniently employed are spunbond and meltblown processes, from which the nonwoven fabrics can directly be formed.

Spunbond fibers are generally produced by extruding a molten polymer through a large spinneret having several thousand holes per linear meter or from banks of smaller spinnerets, for example, containing as few as 40 holes. After exiting the spinneret, the molten fibers are quenched by a cross-flow air quench system, then pulled away from the spinneret and attenuated by high speed air. Lay-down of the filaments to create a nonwoven layer occurs on a permeable transport belt. Spunbond fibers are generally continuous and range in fiber diameter between ca. 10-100 μm.

Meltblown fibers on the other hand are generally much smaller in diameter and usually range between 0.5-10 μm. Additionally, meltblown fibers are considered to be mainly discontinuous.

A meltblowing process is a process in which fibers are formed by extruding a molten thermoplastic material through a plurality of fine, usually circular, die capillaries as molten threads or filaments into a high velocity, usually heated, gas streams which attenuate the filaments of molten thermoplastic material to reduce their diameter. The meltblown process normally has the filaments in single row of filaments across the width of the die. Thereafter, the meltblown fibers are carried by the high velocity gas stream and are deposited on a collecting surface to form a web of randomly dispersed meltblown fibers. Meltblown fibers are microfibers which may be continuous or discontinuous.

The nonwoven fabric in accordance with the invention can additionally be treated to add specific properties. Most common are topical treatments to make the fabric either hydrophilic or to make it hydrophobic. Most common is the treatment of the fabric with either hydrophilic surfactants or with a silicon material. In the context of the present invention a surface of a nonwoven fabric or nonwoven web is "hydrophilic" when the contact angle of water disposed on that surface is less than about 90 and a surface is "hydrophobic" when the contact angle of water disposed on that surface is greater than or equal to 90.

The nonwoven fabric according to the invention can consist of only one type of fibers or fiber layers, e.g. a spunbond layer, but it suitably can comprise additional nonwoven layers which may differ from each other. Suitable multi-layer fabrics may include one or more spunbond layers (S) and meltblown layers (M), such as SMS, SMMS, SSMMS, etc. adhered to a nonwoven fabric according to the present invention. Usually, these multilayer fabrics are made in one step on a single line with multiple beams, which generally encompass a combination of spunbond and meltblown beams. In some cases it might be advantageous or technically necessary to make a multiple layer according to the invention in two or more separate steps.

The use of spunbond layers that differ in their fiber cross-section or in their fiber type are possible. Thus, it is also possible to combine a layer of trilobal filaments with a layer of round fibers, or to combine a core-sheath bicomponent layer with a side-by-side biocomponent layer.

In case the nonwoven fabric contains an additional nonwoven web, the additional may have a basis weight in the range between 5-80 grams/m$^2$, preferably in the range of from 6-50 grams/m$^2$.

The nonwoven fabric in accordance with the present invention can suitably be used in absorbent articles such as disposable absorbent articles selected from the group consisting of hygiene articles, incontinence articles, diapers, wipes and fem-care articles. Suitable disposable absorbent articles in which the present nonwoven can be used include those selected from the group consisting of baby diapers, pull-ups, training pants, hygiene closure systems, adult incontinence briefs and diapers, panty liners, sanitary napkins, medical garments, and bandages. Suitable wipes can comprise wet and dry wipes for hygiene and home care, cleaning wipes, industrial wipes, oil absorbing wipes, and the like.

Disposable absorbent articles are absorbent articles which are not intended to be laundered or otherwise restored or reused as absorbent articles. Generally, such absorbent articles comprise a back sheet, a top sheet and an absorbent core which is arranged between the back sheet and the top sheet. An additional function of the top sheet is to provide skin comfort.

The present invention also relates to a process for forming the present nonwoven fabric.

Accordingly, the present invention also relates a process for forming a nonwoven fabric comprising the steps of:
(a) forming a nonwoven web of polypropylene-containing fibers that in addition contain a slip agent; and
(b) feeding the nonwoven web into a nip defined between oppositely positioned first and second rolls, whereby at least one of the rolls has a patterned outer surface to apply a bonding pattern to the first nonwoven web, whereby the bonding pattern comprises the alternating pattern which consists of the individualized bonded areas and the non-bonded area as defined hereinbefore.

Further, the present invention also relates to a process for forming a nonwoven fabric according to claim 11 comprising the steps of:
(a) forming a first nonwoven web;
(b) forming a second nonwoven web;
(c) forming a third nonwoven web;
(d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern which consists of bonded areas and the non-bonded area as defined hereinbefore; and
(e) bonding the first, second and third nonwoven web together to form the nonwoven fabric.

Preferably, in these processes the forming of at least one of the three nonwoven webs is carried out by means of a spunbond process or a meltblown process.

The rolls to be used in the processes according to the present invention are suitably right circular cylinders that can be formed of any suitable, durable material. Such rolls will be operated in ways known in the art.

The locations of the oppositely positioned rolls can suitably be varied to form the nip between the rolls. The nip pressure within nip can suitably be varied depending upon the properties of the one or more nonwoven webs to be processed. The same is true for the necessary temperature of the calender rolls, which has to be adjusted according to the required final properties and the kind of fibers to be bonded.

The bonded areas are suitably formed by means of melt-fusing by controlling the temperature of at least one of the rolls. The temperature of the outer surface of at least one of the rolls can be adjusted by heating or cooling the rolls. The heating and cooling may affect the features of the web(s) being processed and the degree of bonding of single or multiple webs being passed through the nip formed between the respective rolls.

One of the rolls to be used will contain a bonding pattern on its outermost surface comprising a continuous pattern of land areas defining a plurality of discrete openings, apertures or holes. Each of the openings in the one or more rolls will form a discrete unbonded area in at least one side of the nonwoven fabric or nonwoven web. The other roll will suitably have an outer surface which is much smoother than the other roll. Preferably, the outer surface of the other roll will be smooth or flat. The rotational speeds of the respective rolls are substantially identical.

Hereafter the invention will be further illustrated by the non-limiting drawing.

In FIG. 1, a side of a nonwoven fabric is shown having an alternating pattern of individualized bonded areas in the form of rods in the cross direction of the web which define a non-bonded area.

EXAMPLES

In order to show the attractiveness of the present invention the tensile strength and the results of the Handle-O-Meter test of a known nonwoven fabric and a nonwoven fabric in accordance with the present invention are compared. The tensile strength is the maximum tensile force (Peak Force) a material will sustain before tensile failure, as measured by the Tensile Strength Measurement Method (WSP 110.4) set forth herein. The Handle-O-Meter test (WSP 90.3) is used to measure softness and stiffness. These tests are well-known standard methods in the non-woven industry. The slip agent used in these Examples was CESA slip PPA 0050079 (commercially available from Clariant).

In Table 1, the results are shown of a 15 gsm polypropylene spunbond fabric in accordance with the present invention and a known 15 gsm polypropylene spunbond.

TABLE 1

|  | standard spunbond fabric; oval elliptic pattern (18.1%) | | spunbond fabric; CD-rod pattern (10.1%) | |
| --- | --- | --- | --- | --- |
|  | no slip additive | with slip additive | no slip additive | with slip additive |
| Tensile strength (N/5 cm) in MD WSP 110.4 | 25 | 26 | 26 | 27 |
| Handle-O-Meter (mN) WSP 90.3 | 56 | 38 | 27 | 16 |

It will be clear from Table 1 that the combination of a CD-rod pattern with a slip agent provides a surprisingly high softness that with known patterns cannot be achieved. The lower the value in the handle-o-meter, the lower is the stiffness, and the less force is needed to deform the fabric. This translates into an increasingly softer feeling.

The invention claimed is:
1. A nonwoven fabric comprising a plurality of polypropylene-containing fibers that form a nonwoven web, which fibers in addition contain a slip agent, the web has a side which is provided with an alternating pattern which consists of individualized bonded areas which are in the form of rod-shaped patterns which are arranged in the cross direction of the web, wherein the rods each in their length direction form an angle of 90° with the machine direction of the web, and the rods are arranged in such a way that in the machine direction of the web no uninterrupted regions exist along the web while in the cross direction of the web the arrangement of the rods defines a plurality of uninterrupted regions that extend continuously along the web, the alternating pattern of individualized bonded areas defines a non-bonded area, the web has a basis weight on the range of from 5-25 g/m², the surface of the bonded areas is in the range of 5-20% of the total surface of the side, and the surface of the non-bonded area is in the range of 80-95% of the total surface of the side.

2. A nonwoven fabric according to claim 1, wherein the surface of the bonded area is in the range of from 8-15% of the total surface area of the side.

3. A nonwoven fabric according to claim 2, wherein the surface of the non-bonded area is in the range of from 85-92% of the total surface area of the side.

4. A nonwoven fabric process according to claim 1, wherein the slip agent is a hydrocarbon compound having one or more functional groups selected from hydroxide, aryls and substituted aryls, alkoxys, carboxylates, esters, amides, an unsaturated C—C bond, oxygen, nitrogen, carboxyl, a fatty acid derivative, or a compound based on a silicone-containing compound.

5. A nonwoven fabric according to claim 1, wherein the fibers have a tex of less than 2.5 dtex.

6. A nonwoven fabric according to claim 1, wherein the cross-section of the fibers is round.

7. A nonwoven fabric according to claim 1, wherein the nonwoven web has a basic weight of 8-22 g/m².

8. A nonwoven fabric according to claim 1 comprising additional nonwoven webs.

9. A nonwoven fabric according to claim 8 comprising one or more spunbond webs and one or more meltblown webs.

10. A process for forming a nonwoven fabric comprising the steps of:
  (a) forming a nonwoven web of polypropylene-containing fibers that in addition contain a slip agent; and
  (b) feeding the nonwoven web into a nip defined between oppositely positioned first and second rolls, whereby at least one of the rolls has a patterned outer surface to apply a bonding pattern to the first nonwoven web, whereby the bonding pattern comprises the alternating pattern which consists of the individualized bonded areas and the non-bonded area as defined in claim 1.

11. A process for forming a nonwoven fabric according to claim 8 comprising the steps of:
  (a) forming a first nonwoven web;
  (b) forming a second nonwoven web;
  (c) forming a third nonwoven web;
  (d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern which consists of bonded areas and the non-bonded area as defined in claim 1; and
  (e) bonding the first, second and third nonwoven web together to form the nonwoven fabric.

12. A process according to claim 10, wherein at least one of the three nonwoven webs is made by means of a spunbond process or a meltblown process.

* * * * *